United States Patent
Choi et al.

(10) Patent No.: US 11,465,118 B2
(45) Date of Patent: Oct. 11, 2022

(54) COMPOSITION FOR PREPARING HOLLOW PARTICLES, HOLLOW PARTICLES USING THE SAME AND METHOD OF MANUFACTURING THE HOLLOW PARTICLES

(71) Applicant: KOREA ADVANCED INSTITUTE OF SCIENCE AND TECHNOLOGY, Daejeon (KR)

(72) Inventors: Insung S. Choi, Daejeon (KR); Hojae Lee, Daejeon (KR); Won Il Kim, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 168 days.

(21) Appl. No.: 16/599,791

(22) Filed: Oct. 11, 2019

(65) Prior Publication Data
US 2020/0114330 A1 Apr. 16, 2020
US 2022/0184576 A9 Jun. 16, 2022

(30) Foreign Application Priority Data

Oct. 2, 2019 (KR) .......................... 10-2019-0121927

(51) Int. Cl.
*B01J 13/18* (2006.01)
*C08G 65/44* (2006.01)

(52) U.S. Cl.
CPC ............. *B01J 13/18* (2013.01); *C08G 65/44* (2013.01)

(58) Field of Classification Search
CPC ........... B01J 13/18; B01J 13/08; C08G 65/44; A61K 8/347; A61K 2800/10; A61K 8/0279; A61K 8/11; A61Q 19/00
See application file for complete search history.

(56) References Cited

FOREIGN PATENT DOCUMENTS

KR 10-2009-0077159 A 7/2009
KR 10-2016-0038835 A 4/2016

OTHER PUBLICATIONS

Biphasic Supramolecular Self-Assembly of Ferric Ions and Tannic Acid across Interfaces for Nanofilm Formation by Kim et al., Advanced Materials, 2017, 29.*
Lee et al., "Iron Gall Ink Revisited: In Situ Oxidation of Fe(II)-Tannin Complex for Fluidic-Interface Engineering", Advanced Materials—8 pages (Oct. 9, 2018).
Lee et al., "Stepwise Assembly of Iron-Tannin Complexes for Liquid-Interface Engineering" (photo)—2 page (Sep. 17-19, 2018).
Kim et al., "Biphasic Supramolecular Self-Assembly of Ferric Ions and Tannic Acid across Interfaces for Nanofilm Formation", Advanced Materials, vol. 29, No. 28, dated Jul. 2017 in 8 pages.
Notice of Allowance in Korean Application No. 10-2019-0121927 dated Aug. 25, 2021 in 2 pages.

* cited by examiner

*Primary Examiner* — Irina S Zemel
(74) *Attorney, Agent, or Firm* — Knobbe Martens Olson & Bear LLP

(57) ABSTRACT

A composition for stably preparing a hollow particle by a coacervation method, a hollow particle prepared using a composition for preparing a hollow particle, and a method of preparing a hollow particle are disclosed. A mono-disperse hollow particle is stably provided by excellent coacervate forming capability, such that it is expected to be beneficially used as a carrier in various fields such as a cosmetic, a paint, plastic, rubber, a synthetic wood, a refractory material, and an agricultural chemical.

15 Claims, 5 Drawing Sheets

PG: Pyrogallol

L-DOPA

CH: Catechin hydrate

ECG: Epigallocatechin gallate

COMPOSITION FOR PREPARING HOLLOW PARTICLES, HOLLOW PARTICLES USING THE SAME AND METHOD OF MANUFACTURING THE HOLLOW PARTICLES

CROSS-REFERENCE TO RELATED APPLICATIONS

This application claims priority under 35 U.S.C. § 119 to Korean Patent Application No. 10-2018-0121774, filed on Oct. 12, 2018 and Korean Patent Application No. 10-2019-0121927 filed Oct. 2, 2019 in the Korean Intellectual Property Office, the disclosure of which is incorporated herein by reference in its entirety.

TECHNICAL FIELD

The following disclosure relates to a composition for stably preparing a hollow particle by a coacervation method, a hollow particle prepared using a composition for preparing a hollow particle, and a method of preparing a hollow particle.

BACKGROUND

A hollow particle includes a spherical particle that is empty inside. The hollow particle has been mainly used to reduce a weight of a product using an empty space present in the inside thereof, or used as a carrier supporting an active ingredient. In general, the hollow particle is prepared from an inorganic material such as silica or an organic material such as an organic polymer, and has been used as a carrier in various fields such as a cosmetic, a paint, plastic, rubber, a synthetic wood, a refractory material, and an agricultural chemical.

The disclosure of this section is to provide background of the invention. Applicant notes that this section may contain information available before this application. However, by providing this section, Applicant does not admit that any information contained in this section constitutes prior art.

SUMMARY

An embodiment of the present invention is directed to providing a new composition for preparing a hollow particle capable of stably preparing the hollow particle by a coacervation method, a hollow particle prepared using a composition for preparing a hollow particle, and a method of preparing a hollow particle.

Specifically, an embodiment of the present invention is directed to providing a composition for preparing a hollow particle and a method of preparing a hollow particle by polymerizing monomers in a mild condition without a separate purification process.

Specifically, an embodiment of the present invention is directed to providing a hollow particle prepared by polymerizing biocompatible monomers by a stable polymerization method without causing a chemical modification of an inner oil phase.

Specifically, an embodiment of the present invention is directed to providing a hollow particle having an inner oil phase with which a hydrophilic polymer is coated and a shape that can be maintained in a continuous phase immiscible with an oil phase.

Specifically, an embodiment of the present invention is directed to providing mono-disperse hollow particles that do not aggregate over time.

In one aspect, there is provided a composition for preparing a hollow particle, the composition containing: a polyphenolic compound; a divalent iron ion; water; and a water-immiscible liquid.

The polyphenolic compound may contain a catechol functional group.

The polyphenolic compound may be one or a mixture of two or more selected from the group consisting tannic acid, gallic acid, pyrogallol, catechin, epigallocatechin, epicatechin, catechin gallate, epigallocatechin gallate, epicatechin gallate, catechol, pyrocatechol, and L-dopa.

The divalent iron ion may be obtained from a ferrous salt source.

The ferrous salt source may be one or a mixture of two or more selected from the group consisting of ferrous sulfate, ferrous hydrochloride, ferrous nitrate, ferrous oxalate, ferrous acetate, ferrous propionate, ferrous citrate, ferrous lactate, ferrous D-gluconate, and a hydrate thereof.

The composition for preparing a hollow particle may form a hollow particle by contact with an oxidant in a range of pH 2.0 to 8.0.

The oxidant may be selected from the group consisting of oxygen and ozone.

The composition may further contain a pro-oxidant, wherein the pro-oxidant aids formation of the hollow particle when being in contact with the oxidant.

An average diameter of the hollow particles may be 100 nm to 500 μm.

The composition may further contain one or a mixture of two or more selected from the group consisting of fatty acid and phospholipid, and an average diameter of the hollow particles may be less than 1 μm.

The water-immiscible liquid may be at least one selected from the group consisting of an oil, a non-aqueous organic solvent, and an oil-soluble bioactive component.

In another aspect, there is provided a method of preparing a hollow particle, the method including: mixing and homogenizing a water-containing continuous phase fluid and a water-immiscible liquid-containing dispersed phase fluid; and sequentially adding a polyphenolic compound and a divalent iron ion while bringing the polyphenolic compound and the divalent iron ion in contact with an oxidant to form a coacervate on an interface formed by stirring the two fluids that are immiscible with each other.

The homogenizing may be performed by further adding one or a mixture of two or more selected from the group consisting of fatty acid and phospholipid.

The homogenizing may be performed by further adding a pro-oxidant.

In still another aspect, a hollow particle includes a core containing a water-immiscible liquid; and a shell formed on the core and containing a complex in which a polyphenolic compound and a ferric ion are chelated, wherein a shell thickness of the hollow particle is ⅟₁,₀₀₀ to ⅟₅₀ based on an average diameter of the hollow particles.

An average diameter of the hollow particles may be 100 nm to 500 μm.

DETAILED DESCRIPTION OF EMBODIMENTS

Figure 1:
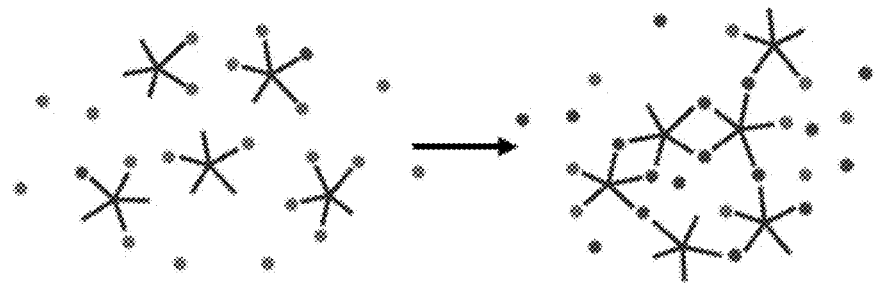
FIG. 1 is a schematic view illustrating a formation of crosslinking of a composition for preparing a hollow particle according to embodiments of the present invention by contact with oxygen.
Figure 1:
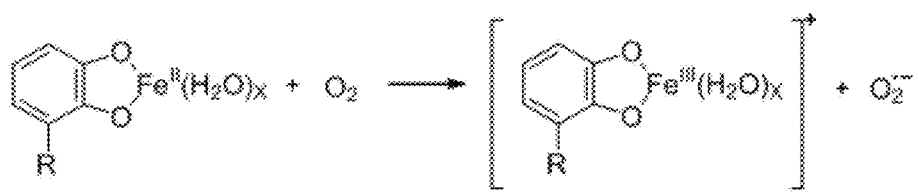

Hereinafter, a hollow particle according to embodiments of the present invention and applications thereof will be described; however, technical terms and scientific terms used herein have the general meaning understood by those skilled in the art to which the present invention pertains unless otherwise defined, and a description for the known function and configuration obscuring the present invention will be omitted in the following description.

The hollow particle may be prepared by various preparation methods such as an emulsion polymerization method, a solvent extraction-evaporation method, a suspension polymerization method, a coacervation method, an extrusion method, and a spray method. Among these preparation methods, a representative method by which a shape of a hollow particle may be easily controlled and the hollow particle may be simply formed is an emulsion polymerization method. However, in a case where a hydrophilic hollow particle is prepared by the emulsion polymerization method, the hydrophilic hollow particle may be easily dissolved in an aqueous dispersion environment during a process or may have undergone complicated processes such as a polymerization process, a swelling process, a core removal process, and a purification process. In particular, polymerization of monomers is required for preparing a shell of a hollow particle, but most monomers are harmful compounds and may cause a specific odor and toxicity even though a trace amount of monomer is contained. Therefore, a strict purification process may be necessary. For such reasons, in order to solve the above, various methods for preparing a hollow particle may be developed; however, it is difficult to develop these methods due to an occurrence of a complicated process or e.g., difficulties in control of a shape of a hollow particle.

The inventors of the present invention have conducted research on a coating technology based on a non-covalent coordination complex, and found that a hollow particle may be provided using a specific composition. In addition, the inventors of the present invention paid attention to the fact that a method of preparing a hollow particle using such a composition is similar to a coacervation method which is one of the various methods of preparing a hollow particle. By deepening the study, the inventors of the present invention completed the present invention to provide a new composition for preparing a hollow particle and applications thereof that may provide a hollow particle by a very simple and stable method based on a non-covalent coordination complex.

The term "coacervation method" herein refers to a method for forming a particle by cohesion of two materials charged with different electric charges at a specific pH or less, or a method in which a particle is naturally formed by interaction of a material with a specific salt ion or alcohol. Here, when the reaction solution is left for a long period of time, the reaction solution is separated into two layers. In this case, a layer in which particles are formed and concentrated refers to a "coacervate layer" and a particle formed by the reaction refers to a "coacervate particle".

In addition, the term "coacervate particle" herein may mean a hollow particle prepared by the coacervation method, and may have the same meaning as that of the hollow particle throughout herein.

In addition, the term "catechol functional group" herein means a functional group derived from a polyphenolic compound represented by Formula $C_6H_4(OH)_2$.

In addition, the term "divalent iron ion" herein means a ferrous ion. In addition, the term "ferric ion" means a trivalent iron ion.

In addition, the term "complex" herein means a complex in which a polyphenolic compound and a ferric ion are chelated, and refers to a "non-covalent coordination complex" containing the polyphenolic compound and the ferric ion.

In addition, the term "particle diameter" means an average diameter of the hollow particles.

The hollow particle are beneficially used as a carrier supporting an active ingredient in various fields. Mass producing coacervate hollow particles using a coating technology based on a non-covalent coordination complex is not provided in the related art.

As described above, the inventors of the present invention have conducted research on a coating technology based on a non-covalent coordination complex, and found that a coacervate hollow particle may be formed through self-assembly of a specific composition, thereby providing the present invention.

The coacervate hollow particle according to embodiments of the present invention not only has a stable structure, but also a thickness of the hollow particle may be easily adjusted by adjusting only a proportion and oxidation time of a divalent iron ion contained in a non-covalent coordination complex. Therefore, it is possible to effectively improve a sealing efficiency of a desired active ingredient. In addition, the coacervate hollow particles according to embodiments of the present invention may be stably dispersed in a formulation at a low apparent density, and may be formulated in various forms.

Hereinafter, a composition for preparing a hollow particle according to embodiments of the present invention will be described.

Specifically, the composition for preparing a hollow particle according to embodiments of the present invention may contain a polyphenolic compound, a divalent iron ion, water, and a water-immiscible liquid.

As illustrated in FIG. 1, the polyphenolic compound and the divalent iron ion of the composition for preparing a hollow particle according to embodiments of the present invention are coordinate-bonded to each other in a solution, thereby forming a non-covalent coordination complex. In this case, the non-covalent coordination complex contained in the composition for preparing a hollow particle according to embodiments of the present invention contains a divalent iron ion, e.g., a ferrous ion.

Figure 2:
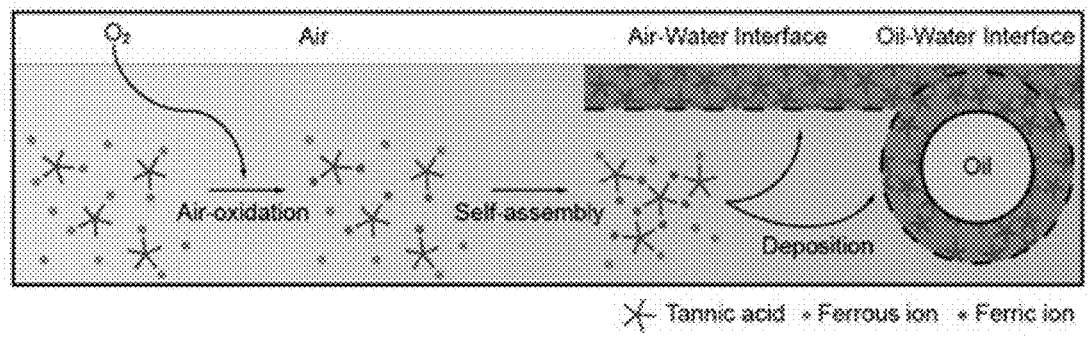
FIG. 2 is a schematic view illustrating a formation of crosslinking of a composition for preparing a hollow particle according to embodiments of the present invention by contact with oxygen and a hollow particle prepared by a coacervation method.

In addition, as illustrated in FIG. 2, self-assembly of the non-covalent coordination complex containing a ferrous ion is induced by being oxidized by contact with an oxidant and converted into a non-covalent coordination complex containing a ferric ion. Accordingly, interfacial polymerization of the non-covalent coordination complex containing a ferric ion is performed on an interface between uniformly dispersed oil and water, thereby forming a hollow particle.

In addition, a thickness growth of the hollow particle may be induced by a continuous coordination bond. Therefore, the thickness of the hollow particle may be appropriately changed depending on the physical properties of a desired hollow particle and the physical properties of an active ingredient to be sealed in the desired hollow particle. In this case, the thickness growth of the hollow particle may be induced by adjusting the proportion and oxidation time of the divalent iron ion. In addition, the thickness growth of the hollow particle may also be adjusted depending on a structure of the polyphenolic compound and a coordination number of the complex.

Figure 3:
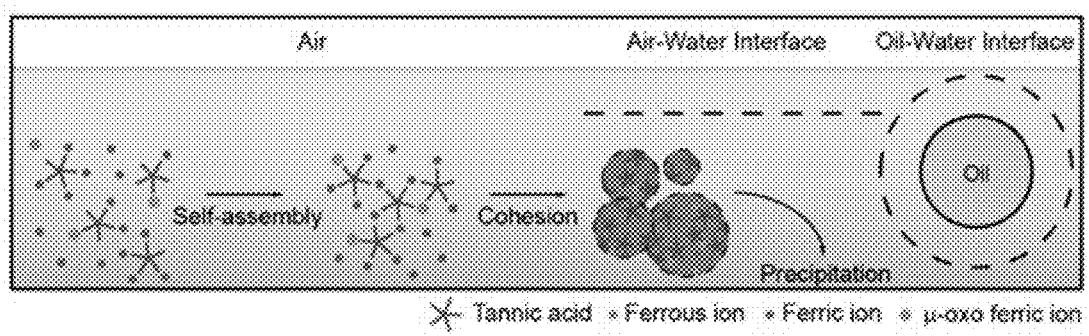
FIG. 3 is a schematic view illustrating a particle prepared by Comparative Example 1 of the present invention.
Figure 4:
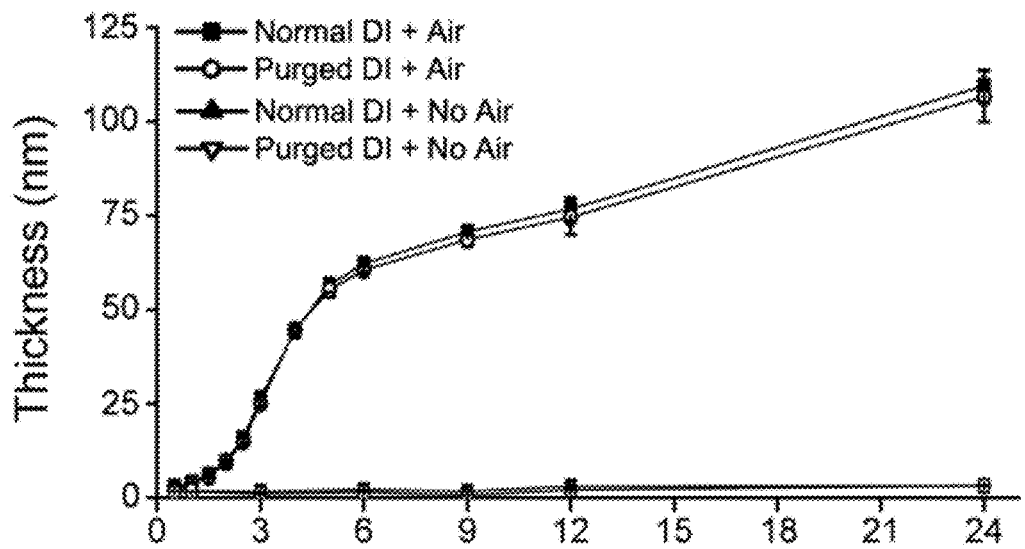
FIG. 4 is a graph illustrating a thickness of a film obtained by applying a composition (Example 1) for preparing a hollow particle according to embodiments of the present invention on a flat gold substrate, and a change in thickness of the film over time depending on the presence or absence of a nitrogen purge of deionized water.

On the other hand, as illustrated in FIG. 3, the non-covalent coordination complex containing a ferric ion is quickly polymerized and aggregated. Accordingly, the non-covalent coordination complex containing a ferric ion is preferably used in a coating technology applied to an immobile interface of a fine particle or a cell surface, but is not preferably used in formation of a hollow particle by interfacial polymerization as in embodiments of the present invention. In embodiments, the polymerization of the non-covalent coordination complex containing a ferric ion is differentiated from the polymerization of the non-covalent coordination complex containing a ferrous ion.

Specifically, the composition for preparing a hollow particle according to embodiments of the present invention may provide a hollow particle in which a water-immiscible liquid is sealed. In addition, in a case of using the composition for preparing a hollow particle according to embodiments of the present invention, it is possible to provide a hollow particle prepared by polymerizing biocompatible monomers by a stable polymerization method without causing a chemical modification of the water-immiscible liquid sealed in the hollow particle. In addition, the composition for preparing a hollow particle according to embodiments of the present invention is useful in terms of preparing a stable hollow particle with only a mild ambient oxidant.

The water-immiscible liquid is not limited as long as it is a non-aqueous liquid which is a liquid immiscible with water typically used in the fields such as a cosmetic, a paint, plastic, rubber, a synthetic wood, a refractory material, and an agricultural chemical.

As an example, the water-immiscible liquid may be one or two or more oils selected from the group consisting of hydrocarbon-based oils such as squalene and mineral oil; higher fatty alcohol-based oils such as cetyl alcohol, stearyl alcohol, behenyl alcohol, 2-octyldodecanol, and isocetyl alcohol; glyceride-based oils such as caprilic/capric triglyceride; silicone-based oils such as phenyl trimethicone, cyclomethicone, dimethicone, cyclopentasiloxane, and decamethylcyclopentasiloxane; ester-based oils such as isopropyl palmitate, 2-octyldodecyl myristate, isopropyl myristate, butyloctyl salicylate, cetyl octanoate, cetyl octylhexanoate, coco-caprylate/caprate, decyl cocoate, isostearyl isostearate, pentaeryrhrityl tetraethylhexanoate, and dicaprylyl carbonate; vegetable oils such as soy oil, castor oil, olive oil, jojoba oil, avocado oil, macadamia oil, meadowfoam seed oil, Shea butter oil, mango butter oil, theobroma grandiflorum seed butter oil, refined grapeseed oil, rosehip oil, saflower oil, peach kernel oil, sunflower seed oil, hempseed oil, rosemary oil, peppermint oil, ylang oil, and argan oil; animal oils such as mink oil, horse oil, and fish oil; and fluorine-based oils such as perfluoropolyether phosphate.

As an example, the water-immiscible liquid may be a non-aqueous organic solvent.

As an example, the water-immiscible liquid may be an oil-soluble bioactive component, and as a specific and non-limiting example, the oil-soluble bioactive component may be at least one selected from the group consisting of retinol, retinoic acid, tocopherol, vitamin D, idebenone, coenzyme Q10, oleanolic acid, ursolic acid, diacetyl boldine, and lipophilic derivatives thereof, but is not limited thereto.

In the case of the oil-soluble bioactive component, changes in color and odor, and reduction of titer occur by oxygen or moisture in air, resulting in insignificant effects. However, in a case where the oil-soluble bioactive component is sealed in the hollow particle according to embodiments of the present invention, it is possible to effectively reduce such occurrences discussed above. In addition, retinol or a derivative thereof induces skin irritation even when used in a small amount. Therefore, they have been used in the field of a cosmetic material applied on the skin at an extremely limited dosage. However, in a case where retinol or a derivative thereof is sealed in the hollow particle according to embodiments of the present invention, it is possible to significantly reduce skin irritation, resulting in expectation of commercialization in the future.

As an example, the water-immiscible liquid may be a mixture of two or more selected from the oil, the non-aqueous organic solvent, and the oil-soluble bioactive component.

As an example, the water-immiscible liquid may be a mixture selected from at least one of each of the oils and the non-aqueous organic solvents.

The polyphenolic compound may contain a catechol functional group.

The polyphenolic compound may contain at least two hydroxyl groups.

The polyphenolic compound contains a catechol functional group and may contain an alicyclic ring system, an aromatic ring system, or a fused ring system thereof.

As an example, the polyphenolic compound may be one or a mixture of two or more selected from the group consisting tannic acid, gallic acid, pyrogallol, catechin, epigallocatechin, epicatechin, catechin gallate, epigallocatechin gallate, epicatechin gallate, catechol, pyrocatechol, and L-dopa.

As an example according to the present invention, a polyphenolic compound containing a plurality of catechol functional groups may be preferable, in terms of inducing the thickness growth by a continuous coordination bond.

As an example, the polyphenolic compound containing a catechol functional group may be a monomer compound having a molecular weight of 2,000 g/mol or less.

As an example, the polyphenolic compound containing a catechol functional group may be a monomer compound having a molecular weight of 200 to 1,800 g/mol.

As an example, the polyphenolic compound containing a plurality of catechol functional groups may be a monomer compound having a molecular weight of 500 to 1,800 g/mol.

As an example, in a case of using the polyphenolic compound containing a plurality of catechol functional groups and selected from the group consisting of tannic acid, epicatechin, catechin gallate, epigallocatechin gallate, and epicatechin gallate, a large thickness of the hollow particle may be implemented in short time.

However, in a case of using the polyphenolic compound having a molecular weight of more than 2,000 g/mol, a hydrogel particle is formed by a non-covalent coordination bond, rather than a hollow particle, which is not preferable. In a case of using a polymer compound whose backbone is covalently bonded to a polyphenolic compound, it may cause e.g., toxicity, which is not biocompatible.

As an example according to the present invention, the polyphenolic compound containing a catechol functional group may have a form of a non-covalent coordination complex containing a ferrous ion in a solution. Thereafter, the non-covalent coordination complex containing a ferrous ion is converted into a non-covalent coordination complex containing a ferric ion through crosslinking by oxidation, and a solid hollow particle is thus formed.

The hollow particle according to embodiments of the present invention includes a non-covalent coordination complex formed on an interface of a droplet of a water-immiscible liquid. Specifically, a polymer structure capable of self-assembling is formed by oxidation and interfacial polymerization of a polyphenolic compound and a divalent iron ion, and the hollow particle is prepared using the polymer structure as a template for forming a hollow particle. In embodiments, the morphology of the hollow particle may be determined by oxidation and interfacial polymerization of a polyphenolic compound and a divalent iron ion.

In the composition for preparing a hollow particle, the divalent iron ion may be obtained from a ferrous salt source.

The ferrous salt source may be one or a mixture of two or more selected from the group consisting of ferrous sulfate, ferrous hydrochloride, ferrous nitrate, ferrous oxalate, ferrous acetate, ferrous propionate, ferrous citrate, ferrous lactate, ferrous D-gluconate, and a hydrate thereof.

The composition for preparing a hollow particle according to an embodiment of the present invention may contain 0.001 to 2 wt % of a polyphenolic compound; 0.01 to 5 wt % of a ferrous salt source; 1 to 50 wt % of a water-immiscible liquid; and residual water, based on the total weight of the composition. Specifically, the composition for preparing a hollow particle may contain 0.001 to 1 wt % of a polyphenolic compound; 0.01 to 3 wt % of a ferrous salt source; 5 to 40 wt % of a water-immiscible liquid; and residual water, based on the total weight of the composition. More specifically, the composition for preparing a hollow particle may contain 0.001 to 0.5 wt % of a polyphenolic compound; 0.01 to 2 wt % of a ferrous salt source; 10 to 30 wt % of a water-immiscible liquid; and residual water, based on the total weight of the composition.

In the composition for preparing a hollow particle according to an embodiment of the present invention, a thickness of the hollow particle may be adjusted by adjusting a mole ratio of the ferrous salt source to the polyphenolic compound.

As an example, the composition for preparing a hollow particle may contain 1 to 1,000 moles of a ferrous salt source, based on 1 mole of the polyphenolic compound. Specifically, 1 to 500 moles of the ferrous salt source may be contained, and more specifically, 1 to 300 moles of the ferrous salt source may be contained.

As an example, it is preferable that the composition for preparing a hollow particle contains 1 to 50 moles of a ferrous salt source, based on 1 mole of the polyphenolic compound.

As an example, it is preferable that the composition for preparing a hollow particle contains 1 to 10 moles of a ferrous salt source, based on 1 mole of the polyphenolic compound.

In addition, the thickness of the hollow particle may also be appropriately adjusted depending on a molecular weight and a pH condition of the non-covalent coordination complex containing a ferrous ion, the type of oxidant, and reaction time with an oxidant.

As described above, the composition for preparing a hollow particle according to an embodiment of the present invention forms a hollow particle by contact with an oxidant. In this case, a pH of the composition may be in a range of 2.0 to 8.0, specifically, in a range of 2.5 to 5.5, and more specifically, in a range of 3.0 to 4.5.

The oxidant may be selected from the group consisting of oxygen and ozone. In this case, the oxidant may be air or oxygen in air.

In addition, the composition for preparing a hollow particle may form a hollow particle by exposure to and contact with the oxidant, e.g., oxygen and ozone, or a combination thereof.

As an example, the exposure to and contact with oxygen, ozone, or a combination thereof may be performed for 0.5 to 60 hours, specifically, 1 to 48 hours, and more specifically, 6 to 24 hours. In this case, the contact may be performed in a state in which oxygen, ozone, or a combination thereof is in the atmosphere.

In addition, the composition for preparing a hollow particle may form a hollow particle by contact in which oxygen, ozone, or a combination thereof is purged into the composition in a gas state.

As an example, in a case where the oxidant such as oxygen and ozone is purged into the composition in a gas state, 10 to 1,000 standard cubic centimeters per minute (sccm) of the oxidant may be injected.

In addition, the residual water which may correspond to a continuous phase of the composition for preparing a hollow particle may be used after being purged with an inert gas (for example, argon, nitrogen, and the like). However, in a case where deionized water is used as a continuous phase, influence of residual water is insignificant.

The composition for preparing a hollow particle according to an embodiment of the present invention may further contain an additional pro-oxidant, in terms of promoting a reaction of the composition with the oxidant. In this case, the pro-oxidant is not limited as long as it promotes oxidation itself or produces active oxygen species, oxygen, ozone, or hydrogen peroxide.

As an example, the pro-oxidant may be one or two or more selected from the group consisting of compounds such as urea, percarbonate, periodic acid, periodate, perchloric acid, perchlorate, perbromic acid, perbromate, perboric acid, perborate, permanganic acid, permanganate, persulfate, bromate, chlorate, chlorite, chromate, iodate, iodic acid, ammonium persulfate, calcium peroxide, barium peroxide, sodium peroxide, urea peroxide, and benzoyl peroxide; and active oxygen species such as hydrogen peroxide, hydroxy radical, peroxy radical, and superoxide radical. In addition, examples of the compound include alkali metal salts such as potassium salt, sodium salt, and calcium salt, alkaline earth metal salts, and ammonium salts.

As an example, the pro-oxidant may be a source of active oxygen species, and the pro-oxidant may supply active oxygen species from an oxidase selected from the group consisting of glucose oxidase, cholesterol oxidase, and horseradish peroxidase.

As an example, the glucose oxidase produces hydrogen peroxide while decomposing glucose in the presence of glucose.

The pro-oxidant may be contained in an amount of 0.001 to 2 wt %, specifically, 0.01 to 1.0 wt %, and more specifically, 0.01 to 0.2 wt %, based on the total weight of the composition for preparing a hollow particle.

In a case where glucose oxidase is used as a source of the active oxygen species, the glucose may be contained in an amount of 10 to 300 parts by weight, specifically, 50 to 200 parts by weight, and more specifically, 80 to 150 parts by weight, based on 100 parts by weight of the polyphenolic compound. In addition, the glucose and the glucose oxidase may be used at a weight ratio of 30:1 to 10:1, and specifically, 25:1 to 15:1.

The composition for preparing a hollow particle according to an embodiment of the present invention may further contain one or a mixture of two or more selected from the group consisting of fatty acid and phospholipid, in terms of stably forming hollow particles in various forms.

As an example, the fatty acid may be one or two or more selected from lauric acid, myristic acid, palmitic acid, stearic acid, behenic acid, arachidonic acid, palmitoleic acid, oleic acid, erucic acid, and derivatives thereof.

As an example, the phospholipid may be one or two or more selected from glycerophospholipids, sphingophospholipids (phosphosphingolipid), phosphatidic acids (PA), phosphatidylinositols, phosphatidylcholines (PC), phosphoinositides, phosphatidylserines (PS), phosphatidylethanolamines (PE), lecithin, and derivatives thereof.

The fatty acid, the phospholipid, or the mixture thereof may be contained in an amount of 0.001 wt % to 5 wt %, specifically, 0.001 wt % to 3 wt %, and more specifically, 0.001 wt % to 1 wt %, based on the total weight of the composition for preparing a hollow particle.

The hollow particle according to embodiments of the present invention prepared by further containing the fatty acid, the phospholipid, or the mixture thereof may have a submicron-sized average diameter with more stability.

As an example, an average diameter of the hollow particles is 0.1 to 1 μm.

As an example, the average diameter of the hollow particles is 20 to 500 nm.

As an example, the average diameter of the hollow particles is 30 to 300 nm.

An ultrasonic treatment may be performed on the composition for preparing a hollow particle according to an embodiment in order to prepare a hollow particle having a smaller diameter.

As an example, the ultrasonic treatment may be performed with an ultrasonic waves of 100 to 50,000 Hz for 1 to 10 minutes.

Hereinafter, a hollow particle and a method of preparing the same according to embodiments of the present invention will be described.

The hollow particle according to an embodiment of the present invention may be a hollow particle in which a water-immiscible liquid is sealed or a hollow particle from which a water-immiscible liquid is removed.

Self-assembly of a non-covalent coordination complex containing a ferrous ion is induced by being oxidized and converted into a non-covalent coordination complex containing a ferric ion, thereby forming a hollow particle according to an embodiment of the present invention. In addition, four-coordinate complex or six-coordinate complex is formed, such that a more stable hollow particle may be provided.

Specifically, the hollow particle may include a core containing a water-immiscible liquid, and a shell formed on the core and containing a complex in which a polyphenolic compound and a trivalent iron ion are chelated.

The hollow particle may be prepared by a preparation method including: mixing and homogenizing a water-containing continuous phase fluid and a water-immiscible liquid-containing dispersed phase fluid; and sequentially adding a polyphenolic compound and a divalent iron ion while bringing the polyphenolic compound and the divalent iron ion in contact with an oxidant to form a coacervate on an interface formed by stirring the two fluids that are immiscible with each other.

As described above, since the hollow particle according to embodiments of the present invention may be oxidized by exposure to and contact with air, it is preferable that the homogenizing is performed under an inert atmosphere environment. In this case, the inert atmosphere environment may be an environment filled with a nitrogen gas or an argon gas.

In addition, in the homogenizing, one or a mixture of two or more selected from the group consisting of fatty acid and phospholipid may be further added, or an ultrasonic treatment may be performed at the same time.

As an example, the adding of one or a mixture of two or more selected from the group consisting of fatty acid and phospholipid may be performed in the mixing of a water-containing continuous phase fluid and a water-immiscible liquid-containing dispersed phase fluid or in the homogenizing.

As an example, it is preferable that the ultrasonic treatment is performed in the mixing of a water-containing continuous phase fluid and a water-immiscible liquid-containing dispersed phase fluid.

As an example, the hollow particle may be formed by induction of a self-assembly of a composition on a surface of an oil uniformly dispersed in water which is a continuous phase. The formed hollow particle may have an oil sealed therein. In this case, the oil may further contain an oil-soluble bioactive component.

As an example, the hollow particle may be formed by induction of a self-assembly of a composition on a surface of an organic solvent uniformly dispersed in water which is a continuous phase. After the hollow particle is formed, the organic solvent sealed in the hollow particle may be dried and removed while being stirred in an aqueous phase, and the dried hollow particle may be a hollow particle that is empty inside.

An average diameter of the hollow particles may be 100 nm (0.1 µm) to 500 µm, specifically, 1 µm to 300 µm, more specifically, 3 µm to 200 µm, and most specifically, 5 to 50 µm.

In addition, the hollow particle according to an embodiment of the present invention satisfies the average diameter described above, and a degree of distribution may be 5.0 or less, specifically, 0.1 to 5.0, and more specifically, 0.5 to 4.5.

The hollow particle may further contain fatty acid, phospholipid, or a combination thereof and may be prepared in various forms. Accordingly, a diameter and a shape of a microstructure of the hollow particle according to embodiments of the present invention may be variously adjusted by adjusting respective components and a component ratio thereof, and a preparation process. In particular, high dispersibility is imparted to the hollow particle according to embodiments of the present invention by a simple process using a raw material (for example, a liquid immiscible with water or oil, phospholipid, and the like) which is relatively easily obtained, and an emulsion particle having a submicron-sized diameter provides a gravity reduction effect during Brownian motion, such that high stability may be provided during storage of a product without a creaming or precipitation phenomenon.

A thickness of the hollow particle may be easily adjusted by adjusting a mole ratio of the ferrous salt source to the polyphenolic compound.

As an example, a shell thickness of the hollow particle is 1/1,000 to 1/50, and preferable 1/500 to 1/50, based on an average diameter of the hollow particles. In this case, the shell thickness of the hollow particle may be directly confirmed by measuring a thickness of a double layer of the hollow particle from an image obtained by atomic force microscopy (AFM) or indirectly confirmed through ellipsometry (Ellipso Technology Co., Ltd., Korea) by using a thickness of a film obtained by applying a composition on a flat gold substrate as a basic model.

As an example, the shell thickness of the hollow particle may satisfy the above ratio, and may also be 1 to 200 nm, specifically, 5 to 150 nm, more specifically, 10 to 120 nm, and most specifically, 25 to 110 nm.

In addition, the thickness of the hollow particle may also be appropriately adjusted depending on a molecular weight and a pH condition of the non-covalent coordination complex containing a ferrous ion, the type of oxidant, reaction time with an oxidant, and a combination thereof.

The hollow particles according to an embodiment of the present invention may be stably dispersed in various formulations due to a low apparent density, and an active ingredient containing a large amount of oil may be sealed in the hollow particle. In this case, the active ingredient may be a water-immiscible liquid, an oil-soluble bioactive component, and a combination thereof.

The hollow particle according to an embodiment of the present invention may be a hollow particle with which a hydrophilic polymer in which a polyphenolic compound is polymerized is coated, and the hollow particle may have a hydrophilic surface.

As an example, a zeta potential of the hollow particle (measured by Nano ZS-90, manufactured by Malvern Instruments, Ltd.) may be −10 mV to −50 mV when measured in deionized water. In embodiments, as the polyphenolic compound is polymerized and a film of a hollow particle is formed, the hollow particle may have a negative zeta potential, stable dispersibility without addition of a surfactant, and excellent characteristics in which cohesion or precipitation of particles does not occur.

The hollow particle according to an embodiment of the present invention may be a hollow particle having a soft bead shape formed in a solution and may have the hydrophilic surface as described above. Accordingly, in a case where the hollow particle is dried in the atmosphere, the shape thereof may be collapsed, but in a case where the hollow particle is present in water or a water-immiscible liquid, the shape thereof is stably maintained, and the hollow particle may thus be beneficially used as a carrier in various fields.

Hereinafter, applications of a hollow particle according to the present invention will be described.

An aspect of the application of the hollow particle according to the present invention may be a cosmetic composition.

The cosmetic composition according to an embodiment of the present invention may contain the hollow particle according to the present invention. Specifically, various types of water-immiscible liquid may be sealed in the hollow particle.

In the cosmetic composition according to an embodiment of the present invention, one or a mixture of two or more selected from an oil and an oil-soluble bioactive component may be stably sealed in the hollow particle. In addition, stability of the oil-soluble bioactive component may be improved.

As an example, the oil may be one or a mixture of two or more selected from the group consisting of a hydrocarbon-based oil, a higher fatty alcohol-based oil, a glyceride-based oil, a silicone-based oil, an ester-based oil, a vegetable oil, an animal oil, and a fluorine-based oil.

As an example, the oil-soluble bioactive component may be one or a mixture of two or more selected from the group consisting of retinol, retinoic acid, tocopherol, vitamin D, idebenone, coenzyme Q10, oleanolic acid, ursolic acid, diacetyl boldine, and lipophilic derivatives thereof.

As an example, the oil-soluble bioactive component may be one or a mixture of two or more selected from the group consisting of butyl methoxydibenzoylmethane, bis-ethylhexyloxyphenol methoxyphenyl triazine, and diethylamino hydroxybenzoyl hexyl benzoate.

As an example, the oil-soluble bioactive component is an oil-soluble component which is in a solid state at room temperature (25° C.) and may be one or a mixture of two or more selected from the group consisting of butters such as Shea butter and mango seed butter; and waxes such as carnauba wax, candelilla wax, and beeswax. In this case, the oil-soluble bioactive component may be in a dissolved state in the oil described above.

As an example, the oil-soluble bioactive component may be contained in an amount of 0.001 to 1 part by weight, specifically, 0.001 to 0.5 parts by weight, and more specifically, 0.01 to 0.3 parts by weight, based on 100 parts by weight of the oil.

As described above, the cosmetic composition according to an embodiment of the present invention may be formulated for various applications such as ultraviolet ray blocking, whitening, and wrinkle improvement, and is expected to be able to provide a sustained effect as well as exhibition of a desired effect, as the oil-soluble bioactive component is stably sealed in a hollow particle.

In embodiments, in the cosmetic composition according to an embodiment of the present invention, various oil-soluble bioactive components are stably sealed in the hollow particle and may be used as an active ingredient carrier that is applicable to all formulations suitable for a topical application.

The cosmetic composition according to an embodiment of the present invention may be contained in an amount of 0.0001 to 10 wt %, specifically, 0.001 to 5 wt %, and more specifically, 0.01 to 3 wt %, based on the total weight of the hollow particle according to the present invention.

The cosmetic composition may be formulated in a general emulsified formulation and solubilized formulation, e.g., using a commonly known preparation method.

As an example, the cosmetic composition may be formulated in a formulation selected from the group consisting of soft toner, astringent toner, nourishing toner, eye cream, nourishing cream, massage cream, cleansing cream, cleansing foam, cleansing water, powder, essence, and pack.

In this case, the cosmetic composition may further contain suitable additives according to the purpose. Examples of the additives include one or more aqueous additives selected from a stabilizer, an emulsifier, a thickener, a moisturizer, a liquid crystal membrane strengthening agent, a pH regulator, a antibacterial agent, a water-soluble polymer, a coating agent, a metal ion sequestering agent, amino acid, organic amine, polymer emulsion, a pH adjuster, a skin nutrient, an antioxidant, an antioxidant aid, a preservative, and flavoring; and one or more oil additives selected from oils, waxes, a hydrocarbon oil, a higher fatty acid oil, higher alcohol, a synthetic ester oil, and a silicone oil.

In addition, the additive may be contained in an amount of 0.001 to 20 wt %, specifically, 0.01 to 10 wt %, and more specifically, 0.05 to 10 wt %, based on the total weight of the cosmetic compound, but is not limited thereto.

Hereinafter, the present invention will be described in more detail with reference to the following Examples. However, these Examples are only intended to assist the understanding of the present invention and are not intended to limit the scope of the present invention.

Unless otherwise noted herein, a unit of all temperatures is ° C. In addition, unless otherwise noted herein, all Examples are performed at a temperature of 20° C. and an atmospheric pressure of 1 atm.

(Evaluation Method)

Evaluation of Physical Properties of Hollow Particle

The morphology of each of the particles prepared in the following Examples and Comparative Example was observed from images obtained by a scanning electron microscopy (SEM) and atomic force microscopy (AFM). Specifically, the image obtained by SEM was observed by using an FEI Inspect F50 microscope (manufactured by FEI Company, Netherlands) (acceleration voltage: kV), and the image obtained by AFM was observed by using INNOVA-LAMRAM HR800 (manufactured by HORIBA, Ltd., Japan).

In addition, the morphology of each hollow particle observed with confocal laser scanning microscopy (LSM 700, manufactured by Carl Zeiss AG, Germany) after treatment with BSA-Alexa 647 (0.4 mg·mL$^{-1}$, Life Technologies) which is a protein conjugated with a chromophore on the hollow particles prepared in the following Examples and incubating the hollow particles for 15 minutes. In this case, a portion which is exhibited in green corresponds to a hollow particle, and the inside of the hollow particle which is exhibited in red corresponds to a solvent (for example, oil).

In addition, a particle diameter ($D_{50}$) and a degree of distribution of each of the particles prepared in the following Examples and Comparative Example were confirmed by directly measuring the images of 100 more hollow particles obtained by confocal laser scanning microscopy (LSM 700) using Image J.

In addition, a thickness of each of the hollow particles prepared in the following Examples was directly confirmed by measuring a thickness of a double layer of the hollow particle from an image obtained by atomic force microscopy (AFM) or indirectly confirmed through ellipsometry (Ellipso Technology Co., Ltd., Korea) by using a thickness of a film obtained by applying a composition on a flat gold substrate as a basic model.

In addition, an oil-soluble bioactive component sealed in each of the hollow particles prepared in the following Examples was confirmed by measuring an absorbance of the oil-soluble bioactive component using a UV-vis spectroscopy.

Example 1

In a reactor filled with nitrogen, 30 g of hexadecane was dispersed in 100 g of deionized water. To the reactor, tannic acid and $FeCl_2 \cdot 4H_2O$ were sequentially added in a usage amount shown in Table 1 and strongly shaken at a speed of 12,000 rpm while being exposed to air (solution pH=3). After adding the $FeCl_2 \cdot 4H_2O$, the composition for preparing a hollow particle was oxidized by oxygen in air, strongly shaken for 60 seconds, and then was left for 24 hours (solution pH after 24 hours=2).

After the reaction was finished, the prepared hollow particle was washed with deionized water three times.

Figure 5:
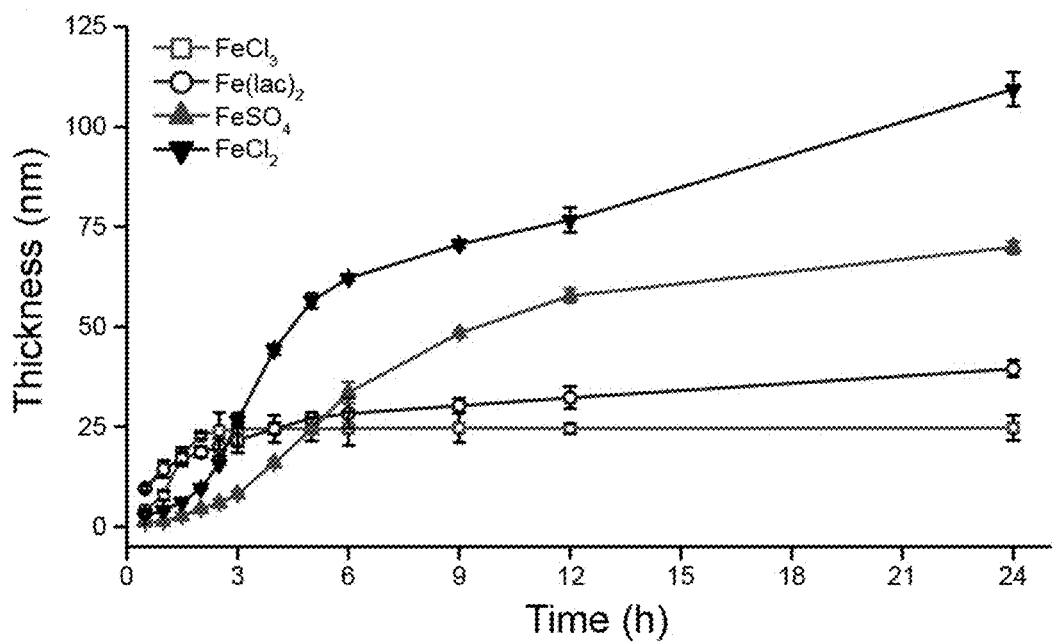
FIG. 5 is a graph illustrating a thickness of films obtained by applying compositions for preparing a hollow particle (Examples 1 to 3) according to embodiments of the present invention and a composition for preparing a hollow particle (Comparative Example 1) on a flat gold substrate.

Physical properties of the hollow particle prepared by the above method were measured by the evaluation method described above, and the results thereof are shown in Table 1 and FIG. 5.

In addition, it was confirmed that the deionized water used in the preparation method was not affected by the presence and absence of a nitrogen purge.

Example 2

A hollow particle was prepared using 0.17 g of tannic acid and 0.28 g of $FeSO_4 \cdot 7H_2O$ instead of $FeCl_2 \cdot 4H_2O$ of Example 1 by the same preparation method as that of Example 1 (1:10).

Physical properties of the hollow particle prepared by the above method were measured by the evaluation method described above, and the results thereof are shown in Table 1 and FIG. 5.

Example 3

A hollow particle was prepared using 0.17 g of tannic acid and 0.24 g of $Fe(lac)_2$ instead of $FeCl_2 \cdot 4H_2O$ of Example 1 by the same preparation method as that of Example 1 (1:10).

Physical properties of the hollow particle prepared by the above method were measured by the evaluation method described above, and the results thereof are shown in Table 1 and FIG. 5.

Example 4

A hollow particle was prepared using 0.13 g of pyrogallol (PG) instead of tannic acid of Example 1 and 0.20 g of $FeCl_2 \cdot 4H_2O$ by the same preparation method as that of Example 1.

Figure 6:
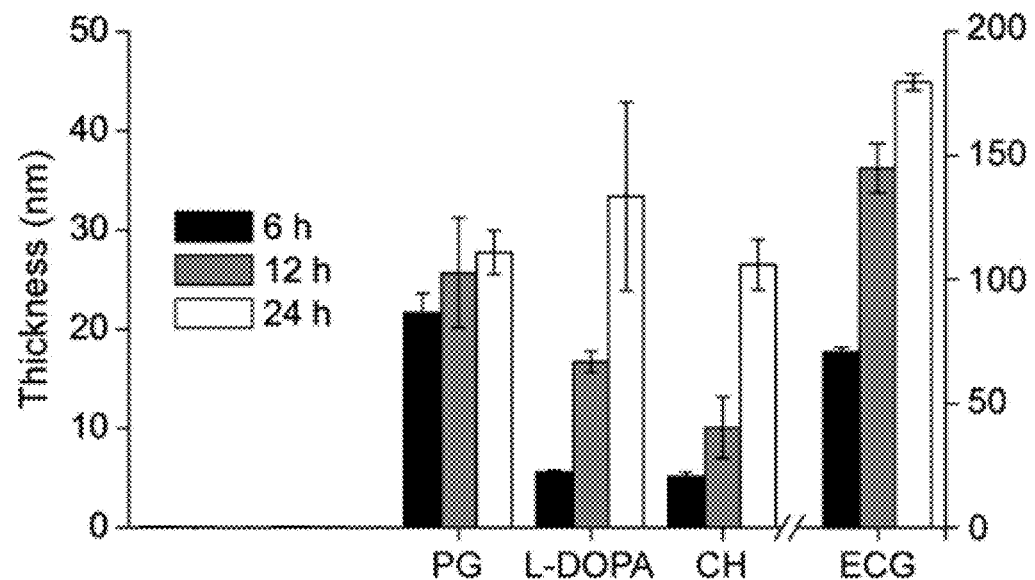
FIG. 6 is a graph illustrating a thickness of films obtained by applying compositions for preparing a hollow particle (Examples 4 to 7) according to embodiments of the present invention on a flat gold substrate.
Figure 6:
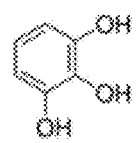
Figure 6:
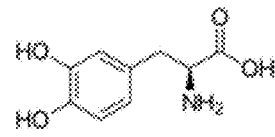
Figure 6:
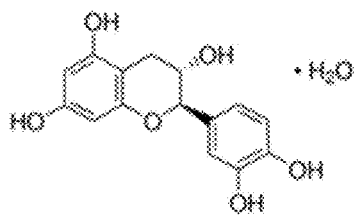
Figure 6:
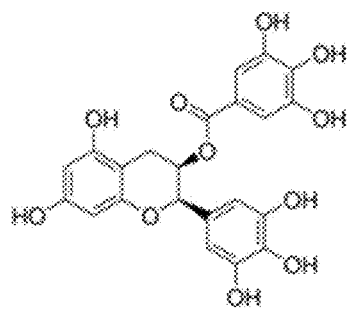

Physical properties of the hollow particle prepared by the above method were measured by the evaluation method described above, and the results thereof are shown in Table 1 and FIG. 6.

Example 5

A hollow particle was prepared using 0.20 g of L-dopa instead of tannic acid of Example 1 and 0.20 g of $FeCl_2·4H_2O$ by the same preparation method as that of Example 1.

Physical properties of the hollow particle prepared by the above method were measured by the evaluation method described above, and the results thereof are shown in Table 1 and FIG. 6.

Example 6

A hollow particle was prepared using 0.29 g of catechin (CH) instead of tannic acid of Example 1 and 0.20 g of $FeCl_2·4H_2O$ by the same preparation method as that of Example 1.

Physical properties of the hollow particle prepared by the above method were measured by the evaluation method described above, and the results thereof are shown in Table 1 and FIG. 6.

Example 7

A hollow particle was prepared using 0.46 g of epigallocatechin gallate (ECG) instead of tannic acid of Example 1 and 0.20 g of $FeCl_2·4H_2O$ by the same preparation method as that of Example 1.

Physical properties of the hollow particle prepared by the above method were measured by the evaluation method described above, and the results thereof are shown in Table 1 and FIG. 6. In FIG. 6, left Y-axis represents a thickness of each of the hollow particle prepared in Examples 4 to 6, and right Y-axis represents a thickness of the follow particle prepared in Example 7.

Example 8

In a reactor filled with nitrogen, 0.5 g of hexadecane was dispersed in 10 g of deionized water. The dispersed hexadecane was strongly pulverized by a sonicator (tip sonicator) at 20,000 Hz and a strength of 50% while being exposed to air. To the reactor, tannic acid and $FeCl_2·4H_2O$ were sequentially added in the same usage amount as that of Example 1 (solution pH=3). After adding the $FeCl_2·4H_2O$, the composition for preparing a hollow particle was oxidized by oxygen in air and was left for 24 hours (solution pH after 24 hours=2).

After the reaction was finished, the prepared hollow particle was washed with deionized water three times.

It was confirmed that the particle diameter ($D_{50}$) of the hollow particle prepared by the above method was 500 nm.

Example 9

In a reactor filled with nitrogen, 0.5 g of hexadecane was dispersed in 10 g of deionized water. To the reactor, 0.15 g of saturated lecithin extracted from soybeans and hydrogenated (phosphatidylcholine content: 70 to 75%) was further added, and the solution was strongly pulverized by a sonicator (tip sonicator) at 20,000 Hz and a strength of 50% while being exposed to air. To the reactor, tannic acid and $FeCl_2·4H_2O$ were sequentially added in the same usage amount as that of Example 1 (solution pH=3). After adding the $FeCl_2·4H_2O$, the composition for preparing a hollow particle was oxidized by oxygen in air, strongly shaken for 60 seconds, and then was left for 24 hours (solution pH after 24 hours=2).

After the reaction was finished, the prepared hollow particle was washed with deionized water three times.

It was confirmed that the particle diameter ($D_{50}$) of the hollow particle prepared by the above method was 200 nm.

The hollow particle prepared by the above method is used according to a formulation of Table 2 or Table 3 and may be used as a cosmetic composition.

Example 10

In a reactor filled with nitrogen, 0.5 g of hexadecane was dispersed in 10 g of deionized water. To the reactor, 0.15 g of phospholipid extracted from soybeans and hydrogenated (1,2-dioleoyl-sn-glycero-3-phosphocholine) was further added, and the solution was strongly pulverized by a sonicator (tip sonicator) at 20,000 Hz and a strength of 50% while being exposed to air. To the reactor, tannic acid and $FeCl_2.4H_2O$ were sequentially added in the same usage amount as that of Example 1 (solution pH=3). After adding the $FeCl_2·4H_2O$, the composition for preparing a hollow particle was oxidized by oxygen in air, strongly shaken for 60 seconds, and then was left for 24 hours (solution pH after 24 hours=2).

After the reaction was finished, the prepared hollow particle was washed with deionized water three times.

It was confirmed that the particle diameter ($D_{50}$) of the hollow particle prepared by the above method was 150 nm.

Example 11

In a reactor filled with nitrogen, 30 g of ylang oil was dispersed in 100 g of deionized water. To the reactor, tannic acid and $FeCl_2·4H_2O$ were sequentially added in the same usage amount as that of Example 1 (1:10) and strongly shaken at a speed of 12,000 rpm while being exposed to air (solution pH=3). After adding the $FeCl_2·4H_2O$, the composition for preparing a hollow particle was oxidized by oxygen in air, strongly shaken for 60 seconds, and then was left for 24 hours (solution pH after 24 hours=2).

After the reaction was finished, the prepared hollow particle was washed with deionized water three times.

It was confirmed that the particle diameter ($D_{50}$) of the hollow particle prepared by the above method was 12 μm.

Example 12

In a reactor filled with nitrogen, 30 g of an argan oil was dispersed in 100 g of deionized water. To the reactor, tannic acid and $FeCl_2·4H_2O$ were sequentially added in the same usage amount as that of Example 1 (1:10) and strongly shaken at a speed of 12,000 rpm while being exposed to air (solution pH=3). After adding the $FeCl_2·4H_2O$, the composition for preparing a hollow particle was oxidized by oxygen in air, strongly shaken for 60 seconds, and then was left for 24 hours (solution pH after 24 hours=2).

After the reaction was finished, the prepared hollow particle was washed with deionized water three times.

It was confirmed that the particle diameter ($D_{50}$) of the hollow particle prepared by the above method was 9 μm.

Example 13

In a reactor filled with nitrogen, 50 mg of retinol was dispersed in 100 g of deionized water. To the reactor, tannic acid and FeCl$_2$·4H$_2$O were sequentially added in the same usage amount as that of Example 1 (1:10) and strongly shaken at a speed of 12,000 rpm while being exposed to air (solution pH=3). After adding the FeCl$_2$·4H$_2$O, the composition for preparing a hollow particle was oxidized by oxygen in air, strongly shaken for 60 seconds, and then was left for 24 hours (solution pH after 24 hours=2).

After the reaction was finished, the prepared hollow particle was washed with deionized water three times.

It was confirmed that the particle diameter (D$_{50}$) of the hollow particle prepared by the above method was 10 μm.

In addition, a content of retinol sealed in the hollow particle prepared by the above method was confirmed using a UV-vis spectroscopy.

Example 14

In a reactor filled with nitrogen, 30 g of hexadecane was dispersed in 100 g of deionized water. To the reactor, 180 mg of glucose, 10 mg of glucose oxidase, tannic acid, and FeCl$_2$·4H$_2$O were sequentially added in the same usage amount as that of Example 1 (1:10) and strongly shaken at a speed of 12,000 rpm while being exposed to air (solution pH=3). After adding the FeCl$_2$·4H$_2$O, the composition for preparing a hollow particle was oxidized by oxygen in air, strongly shaken for 60 seconds, and then was left for 24 hours (solution pH after 24 hours=2).

After the reaction was finished, the prepared hollow particle was washed with deionized water three times.

It was confirmed that the particle diameter (D$_{50}$) of the hollow particle prepared by the above method was 11 μm.

Comparative Example 1

In a reactor filled with nitrogen, 30 g of hexadecane was dispersed in 100 g of deionized water (nitrogen purge, Purged DI). To the reactor, 0.17 g of tannic acid and 0.27 g of FeCl$_3$·6H$_2$O were sequentially added and strongly shaken at a speed of 12,000 rpm (solution pH=3). After adding the FeCl$_3$·6H$_2$O, the solution was strongly shaken for 60 seconds while being exposed to air, and then was left for 24 hours (solution pH=3).

After the reaction was finished, the prepared hollow particle was washed with deionized water three times.

Physical properties of the hollow particle prepared by the above method were measured by the evaluation method described above, and the results thereof are shown in FIG. 5.

TABLE 2

| Soft toner | Usage amount (g) |
| --- | --- |
| Hollow particle of Example 9 | 0.5 |
| Polyoxyethylene hydrogenated castor oil | 0.5 |
| Glycine | 3.3 |
| Dipotassium Glycyrrhizate | 0.1 |
| 1,3-Butylene glycol | 3.0 |
| Sodium hyaluronate | 0.1 |
| Ethanol | 5.0 |
| Triethanolamine | 0.1 |
| Methyl p-hydroxybenzoate | 0.1 |
| Water | To 100 |

TABLE 3

| Nourishing cream | Usage amount (g) |
| --- | --- |
| Hollow particle of Example 9 | 0.5 |
| 1,3-Butylene glycol | 3.0 |
| Glycerine | 3.0 |
| Hydrogenated Lecithin | 1.0 |
| Octyldodecanol | 3.0 |
| Triethylhexanoin | 2.0 |
| Stearic Acid | 1.5 |
| Cetostearyl Alcohol | 2.0 |
| Polysorbate 60 | 1.5 |
| Sorbitan sesquioleate | 2.0 |
| Dimethicone | 3.0 |
| Xanthan gum | 0.2 |
| Triethanolamine | 0.1 |
| Methyl p-hydroxybenzoate | 0.5 |
| Water | To 100 |

As shown in Table 1, according to the present invention, the hollow particle having a uniform degree of distribution may be provided. In addition, it was confirmed that the thickness of the hollow particle could be easily adjusted by adjusting a ratio of the polyphenolic compound to the divalent iron ion. In particular, it was confirmed that in a case where 10 parts by weight of the divalent iron ion were contained with respect to 1 part by weight of the polyphenolic compound, a significantly decreased thickness of the hollow particle could be realized.

In addition, according to the present invention, it was confirmed that the mono-disperse hollow particle could be provided and the hollow particle having a submicron-sized average diameter could also be very stably provided.

Figure 7:
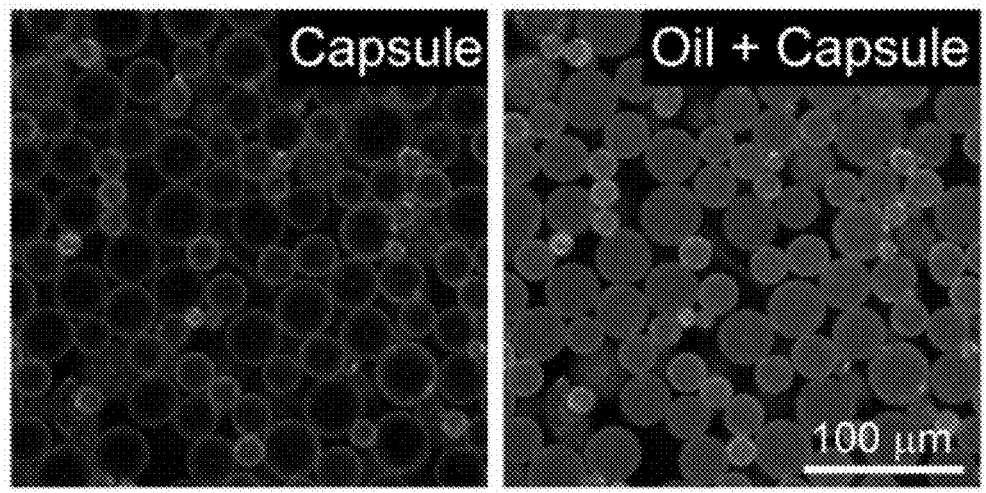
FIG. 7 illustrates images of morphology of a hollow particle observed with confocal laser scanning microscopy (LSM 700) after treatment with BSA-Alexa 647 which is a protein conjugated with a chromophore on the hollow particle prepared using the composition (Example 1) for preparing a hollow particle according to embodiments of the present invention (scale bar: 100 μm).

According to FIG. 7, it was confirmed that hexadecane could be effectively sealed in the hollow particle according to the present invention, and the hollow particle according to the present invention could have uniform morphology of a particle shape having a hollow structure.

Figure 8:
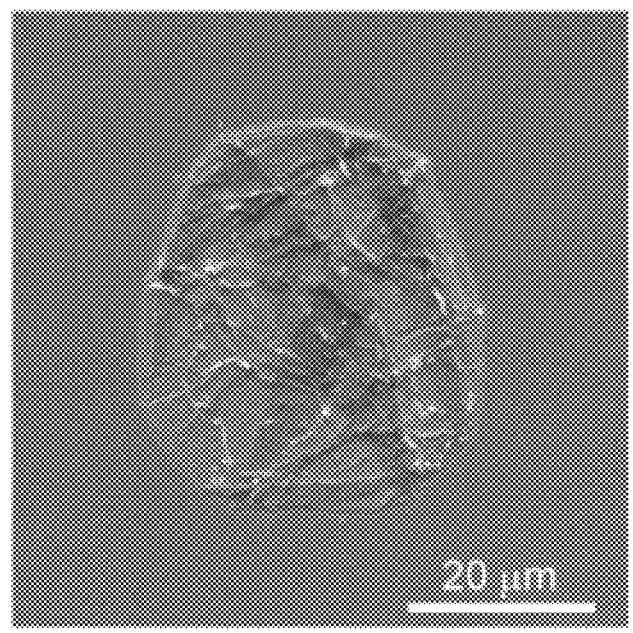
FIG. 8 illustrates an image obtained by observing a hollow particle with scanning electron microscopy (SEM), the hollow particle being obtained by removing an inner oil of the hollow particle prepared using the composition for preparing a hollow particle (Example 1) according to embodiments of the present invention and drying the hollow particle (scale bar: 20 μm).
Figure 9:
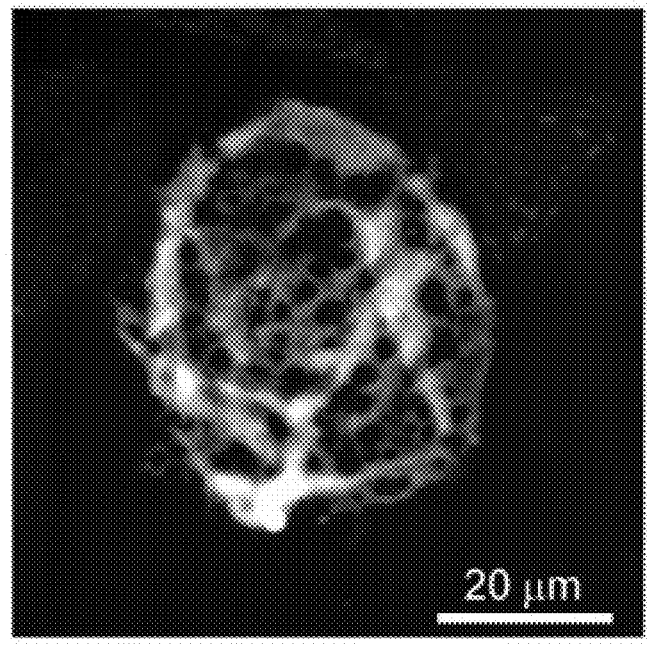
FIG. 9 illustrates an image obtained by observing a hollow particle with atomic force microscopy (AFM), the hollow particle being obtained by removing an inner oil of the hollow particle prepared using the composition for preparing a hollow particle (Example 1) according to embodiments of the present invention and drying the hollow particle (scale bar: 20 μm).

According to FIGS. 8 and 9, it was confirmed that in a case where the inner oil of the hollow particle according to

TABLE 1

| | Example | | | | | | | | | | |
| --- | --- | --- | --- | --- | --- | --- | --- | --- | --- | --- | --- |
| | 1 (TA:Fe(II), mM) | | | | | | | | | | |
| | 0.1:10 | 0.5:10 | 1:5 | 1:10 | 1:50 | 2 | 3 | 4 | 5 | 6 | 7 |
| Thickness (nm) | 65 | 87 | 53 | 106 | 71 | 63 | 33 | 25 | 35 | 25 | 45 |
| Particle diameter (D50, μm) | 6.9 | 6.3 | 6.2 | 6.8 | 6.5 | 6.3 | 7.0 | 6.9 | 6.2 | 6.4 | 6.5 |
| Degree of dispersion (μm) | 3.4 | 4.1 | 3.8 | 3.9 | 3.3 | 3.7 | 4.0 | 4.0 | 3.3 | 3.5 | 4.4 | the present invention was removed and the hollow particle was dried, the hollow particle had a hollow structure of which a shape is collapsed.

In short, the active ingredient containing the water-immiscible liquid may be effectively sealed in the hollow particle according to embodiments of the present invention and may be stably dispersed. Therefore, the hollow particle according to embodiments of the present invention is expected to be beneficially used in various fields such as a cosmetic, a paint, plastic, rubber, a synthetic wood, a refractory material, and an agricultural chemical.

As set forth, according to embodiments of the present invention, the mono-disperse hollow particle may be provided by excellent coacervate forming capability. The water-immiscible liquid such as an oil may be effectively sealed in the hollow particle according to embodiments of the present invention. The hollow particle having a desired thickness may be provided by easily adjusting a degree of crosslinking in the hollow particle through the adjustment of a proportion of the divalent iron ion.

According to embodiments of the present invention, the crosslinking of the composition is formed by oxidation in a state of being exposed to only a mild ambient oxidant, e.g., air, such that a solid hollow particle may be provided. In addition, since the use of a harmful compound causing a specific odor and toxicity may be excluded, the hollow particle is biocompatible and eco-friendly.

Accordingly, the hollow particle according to embodiments of the present invention may be likely to be beneficially used as a carrier in various fields such as a cosmetic, a paint, plastic, rubber, a synthetic wood, a refractory material, and an agricultural chemical, and is expected to be broadly commercialized in the future.

While embodiments of the present invention have been described in detail with reference to specific features, it will be apparent to those skilled in the art that this description is only for embodiments and does not limit the scope of the present invention. Thus, the substantial scope of the present invention will be defined by the appended claims and equivalents thereof.

What is claimed is:

1. A composition for preparing a hollow particle, the composition comprising:
   a polyphenolic compound;
   a divalent iron ion;
   water; and
   a water-immiscible liquid.

2. The composition of claim 1, wherein the polyphenolic compound contains a catechol functional group.

3. The composition of claim 1, wherein the polyphenolic compound is selected from the group consisting of tannic acid, gallic acid, pyrogallol, catechin, epigallocatechin, epicatechin, catechin gallate, epigallocatechin gallate, epicatechin gallate, catechol, pyrocatechol, and L-dopa.

4. The composition of claim 1, wherein the divalent iron ion is obtained from a ferrous salt source.

5. The composition of claim 4, wherein the ferrous salt source is selected from the group consisting of ferrous sulfate, ferrous hydrochloride, ferrous nitrate, ferrous oxalate, ferrous acetate, ferrous propionate, ferrous citrate, ferrous lactate, ferrous D-gluconate, and a hydrate thereof.

6. The composition of claim 1, wherein the composition for preparing a hollow particle forms a hollow particle by contact with an oxidant in a range of pH 2.0 to 8.0.

7. The composition of claim 6, wherein the oxidant is selected from the group consisting of oxygen and ozone.

8. The composition of claim 6, further comprising a pro-oxidant.

9. The composition of claim 1, wherein a diameter of the hollow particle is 0.1 to 500 μm.

10. The composition of claim 1, further comprising one or a mixture of two or more selected from the group consisting of fatty acid and phospholipid.

11. The composition of claim 10, wherein a diameter of the hollow particle is less than 1 μm.

12. The composition of claim 1, wherein the water-immiscible liquid is at least one selected from the group consisting of an oil, a non-aqueous organic solvent, and an oil-soluble bioactive component.

13. A method of preparing a hollow particle, the method comprising:
   mixing and homogenizing a water-containing continuous phase fluid and a water-immiscible liquid-containing dispersed phase fluid; and
   sequentially adding a polyphenolic compound and a divalent iron ion to form the composition of claim 1, wherein sequentially adding the polyphenolic compound and the divalent iron ion is performed while bringing the polyphenolic compound and the divalent iron ion in contact with an oxidant to form a coacervate on an interface formed by stirring the two fluids that are immiscible with each other.

14. The method of claim 13, wherein the homogenizing is performed by further adding one or a mixture of two or more selected from the group consisting of fatty acid and phospholipid.

15. The method of claim 13, wherein the homogenizing is performed by further adding a pro-oxidant.

* * * * *